United States Patent [19]

Campbell et al.

[11] Patent Number: 4,597,299
[45] Date of Patent: Jul. 1, 1986

[54] ION GATE SAMPLE GAS INLET CONTROL FOR GAS CHROMATOGRAPH ANALYZER

[75] Inventors: Donald N. Campbell, Timonium, Md.; Kishore N. Vora, Annandale, Va.; Robert C. Davis, Jr., Westminster, Md.

[73] Assignee: Allied Corporation, Morristown, N.J.

[21] Appl. No.: 709,233

[22] Filed: Mar. 6, 1985

[51] Int. Cl.<sup>4</sup> ............................................. G01N 1/00
[52] U.S. Cl. .................................. 73/864.81; 73/23.1; 250/286
[58] Field of Search ........... 73/864.81, 864.83, 864.84, 73/864.85, 23.1, 863.01; 250/286, 287

[56] References Cited

U.S. PATENT DOCUMENTS 3,845,301 10/1974 Wernlund et al. ............... 250/287
4,390,784 6/1983 Browning et al. ............... 250/286
4,512,181 4/1985 Ayers et al. ............... 73/23.1

*Primary Examiner*—Stewart J. Levy
*Assistant Examiner*—Robert R. Raevis
*Attorney, Agent, or Firm*—Bruce L. Lamb; Robert M. Trepp

[57] ABSTRACT

A gas tight cell receives an unmetered stream of sample gas. The cell is divided into a reaction chamber, as drift chamber and an ion collector chamber by transverse shutter grids normally carrying an ion repellent charge. The inlet of a chromatograph analytical column is connected to the outlet of the cell ion collector chamber. Inert gas admitted to the ion collector chamber is divided into a drift gas stream and into an oppositely directed carrier gas stream. The drift gas flows from the collector chamber through the drift chamber and out the reaction chamber. The carrier gas flows from the collector chamber through a deionizer into the chromatograph column. An electrostatic field urges sample gas ions from the reaction chamber toward the ion collection chamber. The ions are blocked from entering or exiting from the intervening drift chamber by the charge on the shutter grids. At selected times the repellent charges are removed from the shutter grids to allow a group of sample gas ions to traverse the drift chamber and enter the ion collection chamber. Such ions become entrained in the carrier gas stream and are transported thereby through the deionizer into the chromatograph column. The waveform of the current induced in the deionizer by sample gas ions passing therethrough provides information on the time, volume and shape of the gas sample admitted to the chromatograph column.

8 Claims, 3 Drawing Figures

ION GATE SAMPLE GAS INLET CONTROL FOR GAS CHROMATOGRAPH ANALYZER

The present invention relates generally to gas chromatograph analyzers and more particularly to gas sample injection means for gas chromatograph analyzers based on ion mobility detector principles.

BACKGROUND OF THE INVENTION

A gas chromatograph analyzer, as is well known in the art, separates a sample gas into its constituent components by injecting the sample into a carrier gas stream which then moves the sample through a column which contains a stationary liquid supported on a porous packing material. In passing through the column the sample is partitioned into its component compounds which emerge from the column at times dependent upon the compositions of the components. The effluent gas from the column is passed into a detector which senses a change in the characteristic of the gas, such as thermal conductivity, and produces an electrical output accordingly. The detector output is recorded against a time base, usually by means of a strip chart recorder, providing a record of the times elapsing between injection of the sample into the column and the emergence of various components from the column together with peak values indicative of the relative quantities of the components in the sample.

The ability of a gas chromatograph to resolve a sample into its components is dependent in large part upon the speed of injection of the sample into the column and the shape of the sample. Ideally, the sample is in the form of a very narrow plug having flat, sharply defined leading and trailing interfaces with the carrier gas. Conventionally, sample gas is injected into the chromatograph column by an electrically or pneumatically actuated sample valve which momentarily switches the flow path from a carrier gas source into the column inlet so that the carrier gas first passes into a sample chamber and simultaneously switches the sample chamber outlet to the column inlet. After sample injection carrier gas flow is switched back to the column inlet.

The speed of the sample valve operation is obviously limited by its mechanical construction, the inertia of the movable parts thereof and the available actuation force. Limitations upon the opening and closing speed of the sample valve and the valve throttling effect adversely affect the size and shape of the pulse of sample gas entering the chromatograph column, producing generally a broader than desirable sample pulse having interfaces which are distorted by diffusion with the carrier gas. The diffusional boundaries of the sample pulse result in an injection time which is not clearly defined, while excessive breadth of the sample pulse further confuses the precise time of injection of the sample into the column and may introduce a sufficient volume of sample gas into the column to cause saturation of the column stationary phase or saturation of the detector. The resultant chromatogram may then show overlapped peaks which obscure certain components of the sample or complicate the identification thereof. Saturation of the column stationary phase or detector may cause a complete failure of the detector to sense component peaks and further impairs the utility of the analyzer by prolonging the time required to backflush and cleandown the column and the detector.

The present invention eliminates the problems associated with mechanical sample valves in gas chromatograph analyzers by replacing the sample valve with an electronically controlled ion gated which is capable of admitting to the chromatograph column inlet, at a precisely controlled time, a very narrow, sharply defined sample gas pulse of known shape. The sample inlet control of the invention is based upon the principle of an ion mobility detector, an instrument normally used alone for classifying gaseous compounds in accordance with the mobility of ions thereof, which are accelerated by an electric field to a size/mass dependent terminal velocity in a stream of counterflowing drift gas.

A typical ion mobility detector is described in U.S. Pat. No. 3,845,301, there termed a plasma chromatograph, as comprising a gas enclosing cell divided by ion shutter grids into a reaction region, a drift region and a detector region. Sample gas and a readily ionizable reactant gas are introduced into the reaction region where a radioactive source ionizes the reactant gas to produce primary ions. Collisions between the primary ions and sample gas molecules produce product ions. Both the primary ions and the product ions are urged towards the drift region by an electrostatic field established longitudinally of the cell. The ions are blocked from entering the drift region by a first, negatively charged shutter grid. The ion repellant charge is momentarily removed from the first shutter grid and a group of diverse product ions is allowed to enter the drift region. The ions are accelerated through the drift region by an electrostatic field toward the detector region against a counterflowing drift gas stream. In traversing the drift region the product ions become separated into distinct groups which are classifiable by their time of arrival at the detector region. The drift times for the various groups are determined by momentarily removing a negative charge from a second shutter grid located adjacent the ion detector, allowing a particular ion group having a drift time corresponding to the delay between opening the first and second shutter grids to pass to the detector.

The ion mobility detector can provide considerable information concerning the composition of a sample. However, the informatin provided does not characterize the sample components as to charge/mass ratio only, since molecular size has an influence upon the mobility of the ions. To provide further information as to the composition of the sample components, U.S. Pat. No. 3,845,301, referred to above, discloses a plasma chromatograph, i.e. ion mobility detector, arranged to serve as an ion source for a mass spectrograph. The plasma chromatograph operates in the usual manner to produce product ions and to separate those ions into groups according to their mobilities. A particular ion group, selected by the delay time of the opening of the second shutter grid is then passed as an ion beam into the high vacuum of a mass spectrometer where the ions may be more particularly characterized in accordance with the charge/mass ratio thereof.

It is an object of the invention to provide a sample gas inlet control for a gas chromatograph analyzer by which the sample is rapidly injected into the column.

It is a further object of the invention to provide a sample gas inlet control for a gas chromatograph analyzer by which the time of injection of the sample into the chromatograph column is precisely known.

It is still another object of the invention to provide a sample gas inlet control for a gas chromatograph analyzer by which the physical form of the sample injected into the chromatograph column is known.

It is yet another object of the invention to provide a sample gas inlet control for a gas chromatograph analyzer by which the components of a sample gas can be separated as to their mobility characteristics for selective injection of such separated components into the chromatograph column.

BRIEF DESCRIPTION OF THE INVENTION

The invention comprises a sample gas inlet control for a gas chromatograph analyzer wherein the inlet control includes a gas tight cell which receives the sample gas in a more or less continuous stream. The cell is divided into a reaction chamber, a drift chamber and an ion collector chamber by two transverse shutter grids which normally carry an ion repellant charge. Sample gas, which may be mixed with a reactant gas, admitted to the cell reaction chamber becomes ionized, either directly or indirectly, by a radioactive source therein. Ion accelerating electrostatic fields are established in the cell for propelling the ions from the reaction chamber through the drift chamber and out of the collector chamber. At a selected time a shutter grid control momentarily removes the repellant charge from the first shutter grid, allowing a group of ions to enter the drift chamber where the ions separate into groups characterized by their different mobilities against the force of a drift gas flowing in a continuous stream from the collector chamber towards the reaction chamber and venting from the cell at the sample inlet end thereof. The drift gas flowing through the cell proceeds from a gas source connected into the ion collector chamber wherein means divide the total flow from the gas source into two oppositely directed streams, one of which is the drift gas stream, the other of which flows out of the collector chamber through a deionizer and into a chromatograph column as the chromatograph carrier gas stream.

At a selected time after the momentary removal of the repellant charge from the first shutter grid, the shutter grid control momentarily removes the ion repellant charge from the second shutter grid to admit a selected one of the separated ion groups within the drift chamber into the ion collector chamber. The ions are propelled through the collector chamber by the electrostatic field therein, leaving the drift gas stream and entering the carrier gas stream. After entrainment in the carrier gas stream the sample gas ions are swept out of the collector chamber and into the chromatograph column by the carrier gas flow, passing on their way out of the collector chamber through an electrically isolated deionizer. As the sample gas ions pass through the deionizer and surrender their charge an electrical signal is generated which is indicative of the time of entry of the sample into the chromatograph column, and the shape and the quantity of the sample gas entering the column.

DESCRIPTION OF THE DRAWINGS

FIG. 3 is an elevation of a shutter grid subassembly, two of which, when superimposed in oppositely facing directions, comprise a shutter grid used in the invention.

DETAILED DESCRIPTION OF THE INVENTION

Figure 1:
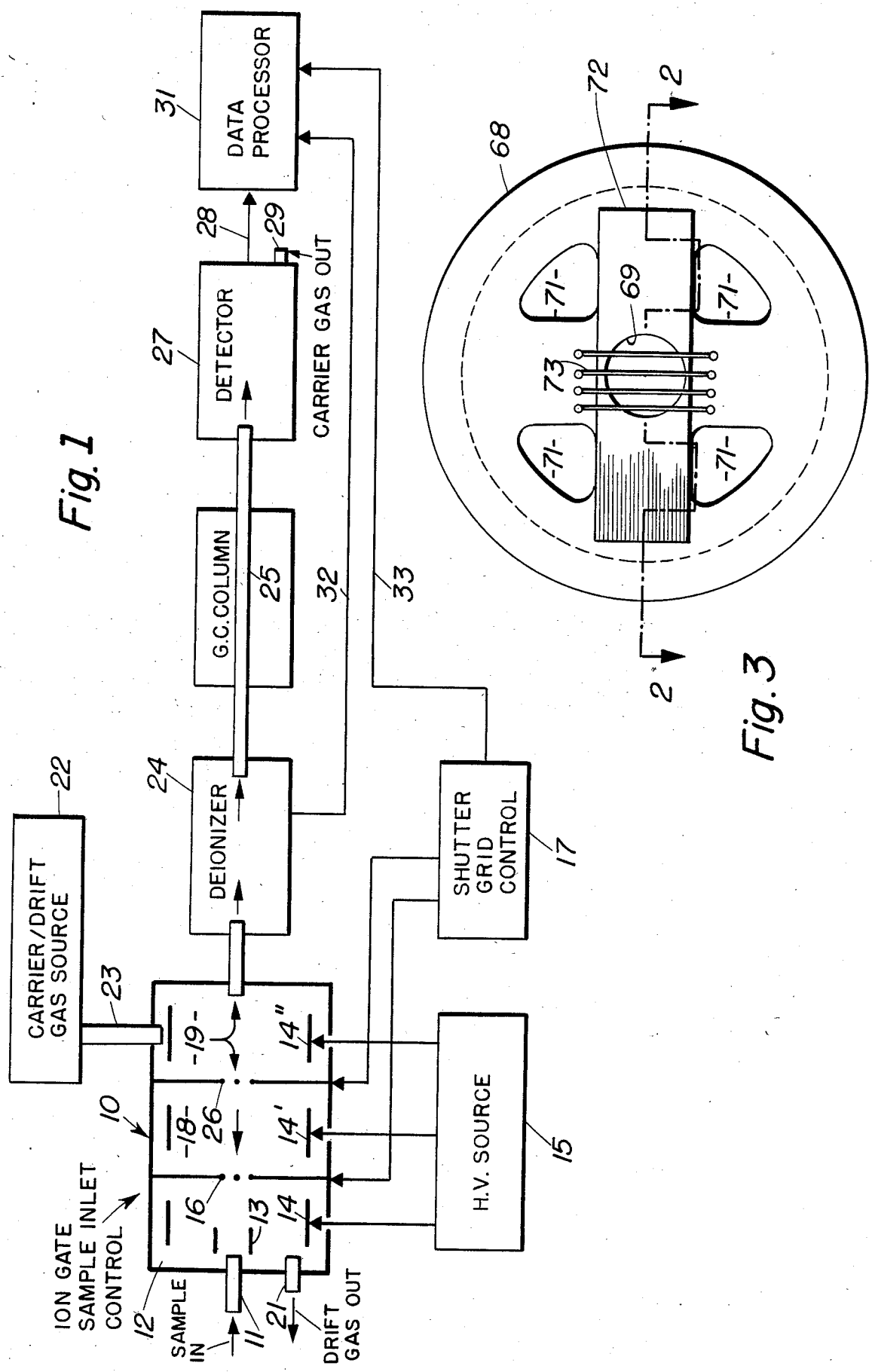
FIG. 1 is a functional block diagram of a gas chromatograph analyzer system incorporating the ion gate sample gas inlet control of the invention.

FIG. 1 illustrates the invention in functional block diagram form. An ion gas sample inlet control 10, operating on the principle of an ion mobility detector described above, receives a stream of sample gas through inlet tube 11 to a reaction chamber 12. A radioactive source 13, such as Ni 63, generates primary and secondary ions within the reaction chamber. The ions are urged in the direction opposite the sample inlet by a progressive electrostatic field established by electrodes 14, 14' and 14" which are energized by a high voltage source 15. The ions are blocked from exiting the reaction chamber by a repelling potential maintained on a first shutter grid 16 by shutter grid control 17. When the repelling potential is momentarily removed from grid 16 by control 17, a group of ions is accelerated from reaction chamber 12 into drift chamber 18. In drift chamber 18, under the influence of the electrostatic field established by electrode 14', the ions are accelerated to a terminal velocity against the force of a drift gas stream which flows continuously from ion collector chamber 19 toward reaction chamber 12, exiting from chamber 12 at outlet 21. The drift gas flow is furnished by a gas source 22 which supplies a stream of inert gas to chamber 19 through inlet 23. Within chamber 19 the gas stream from inlet 23 is divided and a portion of the gas, comprising the ion gas drift gas flows toward outlet 21. The remainder of the gas from inlet 23, comprising the carrier gas for the gas chromatograph column, flows out of chamber 19 through a deionizer 24 into a GC column 25.

Ions traversing through drift chamber 18 become separated into more or less homogeneous groups characterized by their various mobilities against the counter flowing drift gas stream. The ion groups are prevented from exiting chamber 18 by a repelling potential normally maintained on a second shutter grid 26 by shutter grid control 17. After a selected delay from the time of momentarily opening shutter grid 16, control 17 momentarily removes the repelling potential from grid 26 to admit a selected group of ions into collector chamber 19. The ion group admitted to chamber 19 constitutes the gas sample to be analyzed in GC column 25. In chamber 19 the ions are propelled by the electrostatic field established by electrode 14" through that portion of the gas stream from inlet 23 comprising the drift gas stream into that portion of the inlet gas stream comprising the GC carrier gas stream. When entrained in the carrier gas stream the ions pass out of chamber 19 through deionizer 24, which is actually constructed as a part of inlet control 10, and then into GC column 25 where the now deionized sample is separated into its constituent components in traveling through the column. The carrier gas stream and separated sample components flow out of column 25 through a detector 27, which produces an electrical signal on line 28 in response to changes in the characteristics of the gases flowing therethrough. The gases are vented from detector 27 through outlet 29. A data processor 31 receives the signals on line 28 from GC detector 27, together with signals on line 32 from deionizer 24 and synchronizing signals on line 33 from shutter grid control 17 to produce a chromatogram of the sample in accordance with methods known to those skilled in the art. The signals on line 32 are generated by the currents induced in deionizer 24 in the course of deionizing the sample gas inlet pulse passing into column 25. The waveform of the signal output of deionizer 24 is precisely indicative of the time of entry of the sample gas into the GC column and is precisely indicative of the shape or form of such sample. Such information, through the use of known algorithms in data processor 31, enables the data output of detector 27 to be enhanced. The very short time during which shutter grid 26 is open to the passage of sample gas ions, for example, one millisecond, compared with the long time required for the eluted sample components to emerge from the GC column, for example, 10 seconds or greater, results in a chromatogram of very high resolution.

Figure 2:
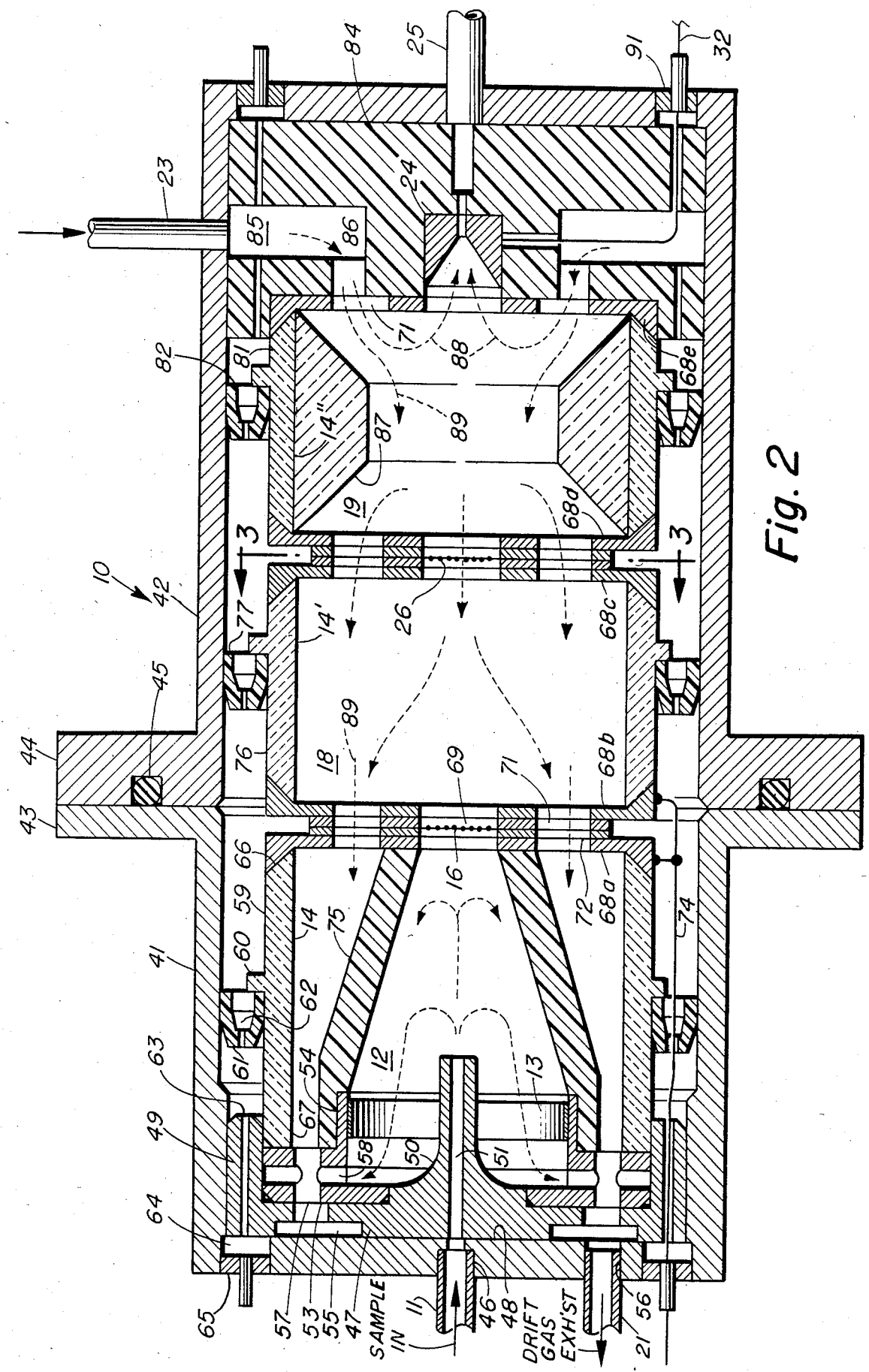
FIG. 2 is a sectional view, along the line 2—2 of FIG. 3, of the ion gate sample gas inlet control of the invention.

The preferred embodiment of the ion gate sample inlet control 10 is illustrated in FIG. 2, to which reference is now made. The control 10 comprises an outer gas-tight shell formed of two mating cup-like sections 41 and 42. The facing ends of sections 41 and 42 are secured together by screws (not shown) passed through the mounting flanges 43, 44 thereon. An O-ring seal carried by flange 44 insures gas-tight integrity for the outer shell when sections 41 and 42 are secured together. A centrally located aperture 46 in the end of shell section 41 has sealed therein the sample gas inlet tube 11. A dish-shaped metal insert 47, the face 48 of which snuggly abuts the inner end wall of shell section 41 and the upstanding rim 49 of which closely engages the inner peripheral wall of shell section 41 is fitted into the end portion of shell section 41. The central portion 50 of insert 47 extends beyond the length of rim 49 and is provided with a bore 51 communicating between shell aperture 46 and the reaction region 12 to permit the entry of sample gas. A metal ring 53 having a protruding neck portion 54 is seated within insert 47. A channel 55 milled in the face of insert 47 communicates with aperture 56 in the end wall of shell section 41. Drift gas outlet 21 is sealed in aperture 56. Holes 57 spaced circumferentially near the outer edge of rim 53 extend through insert 47 to connect channel 55 with the outer peripheral region of reaction chamber 12. Holes 58 drilled radially through ring 53 to intersect holes 57 connect channel 55 with the central interior region of reaction chamber 12. Radioactive source 13 comprising a foil of Ni 63 or other suitable material is secured to the inner wall of ring neck 54. A ceramic cylinder 59 having an outer flange 60 is positioned with the base end 67 thereof in abutment with one face of ring 53 and snuggly fitting within the rim 49 of insert 47. A spacer ring 61 of tetrafluoroethylene resin (TFE) insulating material bears against flange 60, the wall of cylinder 59 adjacent thereto and the inner wall of shell section 41 to maintain cylinder 59 in spaced aligned relationship to shell section 41. Openings 62 penetrate spacer ring 61 in alignment with holes 63 drilled longitudinally through the rim 49 of insert 47. Hole 63 extends to aperture 64 in the end wall of shell section 41. Aperture 64 is sealed by an insulating bushing 65. A number of the openings 62, hole 63 and bushings 65 are spaced circumferencely about the end wall of shell section 41 and the assembly therein to provide for the passage of electrical leads from the exterior of assembly 10 to various contact points within assembly 10.

The inner wall of cylinder 59 is coated entirely with resistive ink, except at the forward chamfered lip 66 and the base end 67, which are coated with conductive ink to establish electrical contact with the resistive ink coating. The resistive ink coating of cylinder 59 comprises electrode 14, which is energized by the high voltage source 15 (FIG. 1) to provide an ion accelerating electrostatic field within reaction chamber 12.

Shutter grid 16 and shutter grid 26 are each formed of two identical superimposed, oppositely facing ring structures 68a and 68b. The outer rim of ring 68a is formed with a tapered lip fitting snuggly with the chamfered end 66 of cylinder 59. Referring to FIG. 3, ring 68 is provided with a central opening 69 and four sectorial openings 71 to permit the flow of drift gas therethrough. An insulating board 72 having a central opening coincident with ring opening 69 extends partially across the face of ring 68. A number of grid wires 73 are stretched over board 72, covering opening 69 and are welded at each end to the face of ring 68. The grid formed by wires 73 is positioned asymmetrically with respect to the center of hole 69, so that when two identical structures of FIG. 3 are superimposed upon one another in oppositely facing directions, the grid covering the coincident openings 69 will be composed of interdigitated grid wires from each structure. Rings 68a and 68b are conductive and both are energized to the same high voltage level by source 15 (FIG. 1) connected thereto via lead 74. Rings 68a and 68b are each separately connected to shutter grid control 17 (FIG. 1) for the application of oppositely polarized control voltages for each ring. The polarities of the voltages of the grid wires extending across opening 69 will thus be alternately positive and negative with respect to the high voltage bias applied by lead 74, thereby forming a repellant field which normally closes opening 69 to the passage of ions. For purposes of clarity, leads connecting rings 68a and 68b to control 17 have been omitted from the drawing.

A generally conically shaped divider 75 of TFE material is fitted at its base end to the neck portion 54 of ring 53 with the forward end thereof abutting ring 68a. Divider 75 tends to reduce the velocity of drift gas flow in the vicinity of the radioactive source 13 and tends to reduce the dispersion of sample gas at the inlet, thereby providing an increase in the time of residence of sample gas in chamber 12 to increase the quantity of productions generated within the chamber. Drift chamber 18 is formed by a flanged ceramic cylinder 76 which is supported in shell section 42 by a TFE spacer ring 77, similar to ring 61. The inner surface of cylinder 76 is coated with resistive ink and the chamfered ends of the cylinder are coated with conductive ink, such coatings comprising electrode 14'. Cylinder 76 is seated between the tapered rim portions of ring 68b and ring 68c of shutter grid 26. The second shutter grid 26, at the forward end of cylinder 76, is constructed identically to shuttered grid 16, previously described. The leads connecting rings 68c and 68d to high voltage source 15 and shutter grid control 17 have been omitted from the drawing for clarity.

Ion collection chamber 19 is formed by a third flanged ceramic cylinder 81 supported by a TFE spacer ring 82. Like cylinder 76, the inner surface of cylinder 81 is coated with resistive ink and the chamfered cylinder ends are conductively coated. Cylinder 81 is seated between the tapered rim portions of ring 68d and ring 68e. Ring 68e is connected to high voltage source 17 for energizing electrode 14'' comprised by the resistive ink coating of cylinder 81. Ring 68e is supported by a channeled cylindrical block 84 of insulating material seated in the closed end of shell section 42. Carrier/drift gas enters shell 42 through inlet 23 and is distributed circularly around block 84 by circular channel 85. Holes 86 spaced along the length of channel 85 enter channel 85 transversely to permit entry of the gas circulating therein through openings 71 in ring 68e to chamber 19. Deionizer 24 comprises a metal insert centrally located in block 84. Insert 24 has a funnel shaped opening therein which communicates with the inlet to GC column 25 sealed in the end of shell section 42. Lead 32 passes through an insulating bushing 91 to connect deionizer 24 with a suitable waveform detector (not shown) in data processor 31 (FIG. 1).

A convergent-divergent insert 87 of TFE material contained within cylinder 81 divides flow of carrier/drift gas entering chamber 19 from channel 85 so that a portion of the gas flows in the direction of arrows 88 to carry the sample gas ion pulse into deionizer 24 and thence through GC column 25. The remainder of the gas flowing into chamber 19 is pinched into a substantially laminar flow in the direction indicated by arrows 89 to flow the length of assembly 10 and exit therefrom via outlet 21. This latter portion of gas comprises the ion gate drift gas.

The invention claimed is:

1. A sample gas inlet control for a gas chromatograph analyzer, said chromatograph including an analytic column and means providing a flow of carrier gas through said analytic column, comprising, means for ionizing said sample gas;
   means for forming said ionized sample gas into a stream;
   means including a shutter grid having an ion repellant electrostatic charge thereon for normally blocking the flow of said ionized sample gas stream;
   means for momentarily removing said ion repellant charge from said shutter grid to permit passage therethrough of a group of ions from said stream;
   means for injecting said group of ions into said chromatograph carrier gas flow; and
   means for deionizing said group of ions in said carrier gas flow prior to entry of said carrier gas flow into said analytic column.

2. Apparatus as claimed in claim 1, with additionally, means associated with said deionizing means for providing an electrical signal corresponding to electrical currents induced in said deionizing means in the course of deionizing said group of ions.

3. Apparatus as claimed in claim 2 wherein said chromatograph includes detector means connected to said analytic column providing data output relating to column effluent and data processing means for processing data output by said detector means, with additionally,
   means for furnishing to said data processing means said electrical signal from said means associated with said deionizing means for use by said data processing means in processing data output of said detector means.

4. A sample gas inlet control for a gas chromatograph analyzer, comprising
   a gas tight cell having an inlet end and an outlet end;
   a shutter grid within said cell dividing said cell into a reaction chamber proximate said inlet end and into a drift chamber proximate said outlet end, said shutter grid normally having an ion repellant electrostatic charge thereon and being pervious to the flow of non-ionized gases;
   a gas chromatograph analyzer column having the inlet end thereof connected into said cell outlet end to receive gas flow from said cell;
   a source of inert gas connected to said cell at said outlet end for supplying a continuous stream of gas to said cell;
   means with said drift chamber for dividing said gas stream from said source into a drift gas stream flowing from said outlet end towards said inlet end and into a carrier gas stream flowing through said outlet end into said chromatograph column;
   means for establishing an electrostatic field within said cell tending to accelerate ions therein in a direction from said inlet end toward said outlet end;
   means at said cell inlet end for admitting sample gas to said cell reaction chamber;
   means at said cell inlet end for venting said drift gas stream to the exterior of said cell;
   means within said reaction chamber for ionizig reactive gases therein;
   means for temporarily removing said ion repellant charge from said shutter grid to permit a group of ions to pass from said reaction chamber into said drift chamber, said ions admitted to said drift chamber accelerating through said drift chamber toward said cell outlet end and becoming entrained in said carrier gas stream; and deionizing means for neutralizing ions entrained in said carrier gas stream, said deionizing means being positioned within said drift chamber at said cell outlet end to receive said carrier gas stream and to conduct said carrier gas stream to said chromatograph column inlet.

5. A sample gas inlet control for a gas chromatograph analyzer as claimed in claim 4, with additionally,
   means for detecting currents induced in said deionizing means during neutralization of ions entrained in said carrier gas stream.

6. A sample gas inlet control for a gas chromatograph analyzer as claimed in claim 5, with additionally,
   a second shutter grid within said drift chamber, said second shutter grid normally having an ion repellant electrostatic charge thereon and being pervious to the flow of non-ionized gases, and
   means for temporarily removing said ion repellant charge from said second shutter grid after a selected delay from the time of removal of said ion repellant charge from said first-mentioned shutter grid.

7. A sample gas inlet control for a gas chromatograph analyzer comprising
   a closed cylindrical shell having an inlet end and an outlet end;
   a plurality of open ended cylinders of insulating material aligned within said shell coaxially therewith and in spaced relationship with the inner wall thereof;
   a coating of electrical resistance material lining the inner wall of each said open ended cylinder;
   a disk-like grid assembly interposed between the abutting ends of each said open ended cylinders, each said grid assembly including a central opening, a plurality of sectorial openings radially spaced from said central opening and a grid of electrical conductors covering said central opening;
   a first generally frusto-conically shaped insert coaxially aligned within the first one of asid open ended cylinders adjacent said inlet end of said shell, the base of said first insert being adjacent said shell inlet end and the apex thereof being in abutment with the periphery of the central opening of the first one of said grid assemblies at the end of said first cylinder;

a second convergently-divergently shaped insert in the last of said open ended cylinders adjacent said shell outlet end;

means for applying an electrical potential to said resistance coating of each said open ended cylinders;

means for admitting sample gas to the interior of said first insert;

means for ionizing sample gas within said first insert;

means at said shell outlet end for admitting a continuous flow of inert gas to the interior of said second insert, said second insert dividing said continuous flow into two streams, the first of said streams being directed toward said shell inlet end, the second of said streams being directed toward said shell outlet end;

means at said shell inlet end for venting said first stream to the exterior of said shell;

means at said shell outlet end for conducting said second stream to the inlet end of a gas chromatograph analytic column;

means for applying an ion repellant electrical potential to said grid of electrical conductors of each of said grid assemblies; and means for selectively removing said ion repellant potential from each said grid of conductors.

8. Apparatus as claimed in claim 7 wherein said means for conducting said second stream includes, means for deionizing gaseous ions contained in said second stream.

* * * * *